United States Patent [19]
Gambini et al.

[11] 3,949,227
[45] Apr. 6, 1976

[54] DEVICE FOR THE PANORAMIC RADIOGRAPHY OF WELDINGS IN METAL PIPINGS

[75] Inventors: Arnaldo Gambini; Giuseppe Cianci, both of San Donato Milanese, Italy

[73] Assignee: Snam Progetti S.p.A., Milan, Italy

[22] Filed: Mar. 25, 1974

[21] Appl. No.: 454,455

Related U.S. Application Data

[63] Continuation of Ser. No. 303,684, Nov. 6, 1972, abandoned, and a continuation of Ser. No. 163,503, July 16, 1971, abandoned, and a continuation of Ser. No. 18,564, March 11, 1970, abandoned.

[30] Foreign Application Priority Data

Mar. 11, 1969 Italy.................................. 13916/69

[52] U.S. Cl............................................. 250/358 P
[51] Int. Cl.²........................................ G01N 23/00
[58] Field of Search................... 250/321, 322, 358; 181/.5 NP; 104/138 R

[56] References Cited
UNITED STATES PATENTS

| | | | |
|---|---|---|---|
| 2,235,928 | 3/1941 | Hardinge | 181/.5 NP X |
| 3,087,058 | 4/1963 | Arvanetakis et al. | 250/321 |
| 3,191,713 | 6/1965 | Green | 181/.5 NP |
| 3,492,477 | 1/1970 | Arnesen | 250/322 |
| 3,547,040 | 12/1970 | Baran | 104/138 R |
| 3,691,385 | 9/1972 | Ketchbaw et al. | 250/321 X |

*Primary Examiner*—Davis L. Willis
*Attorney, Agent, or Firm*—Morgan, Finnegan, Pine, Foley & Lee

[57] ABSTRACT

A self-propelled vehicular radiography device for traveling within a pipeline includes a drive system, having a sensing means responsive to a radiation source on the exterior of the pipeline. The outside source positions a panoramic radiography source carried on the vehicle adjacent the weld to be inspected. Upon removal of the outside source a programmed radiography sequence is commenced. A pendulum steering means is utilized to maintain the device at the bottom of the pipeline.

4 Claims, 3 Drawing Figures

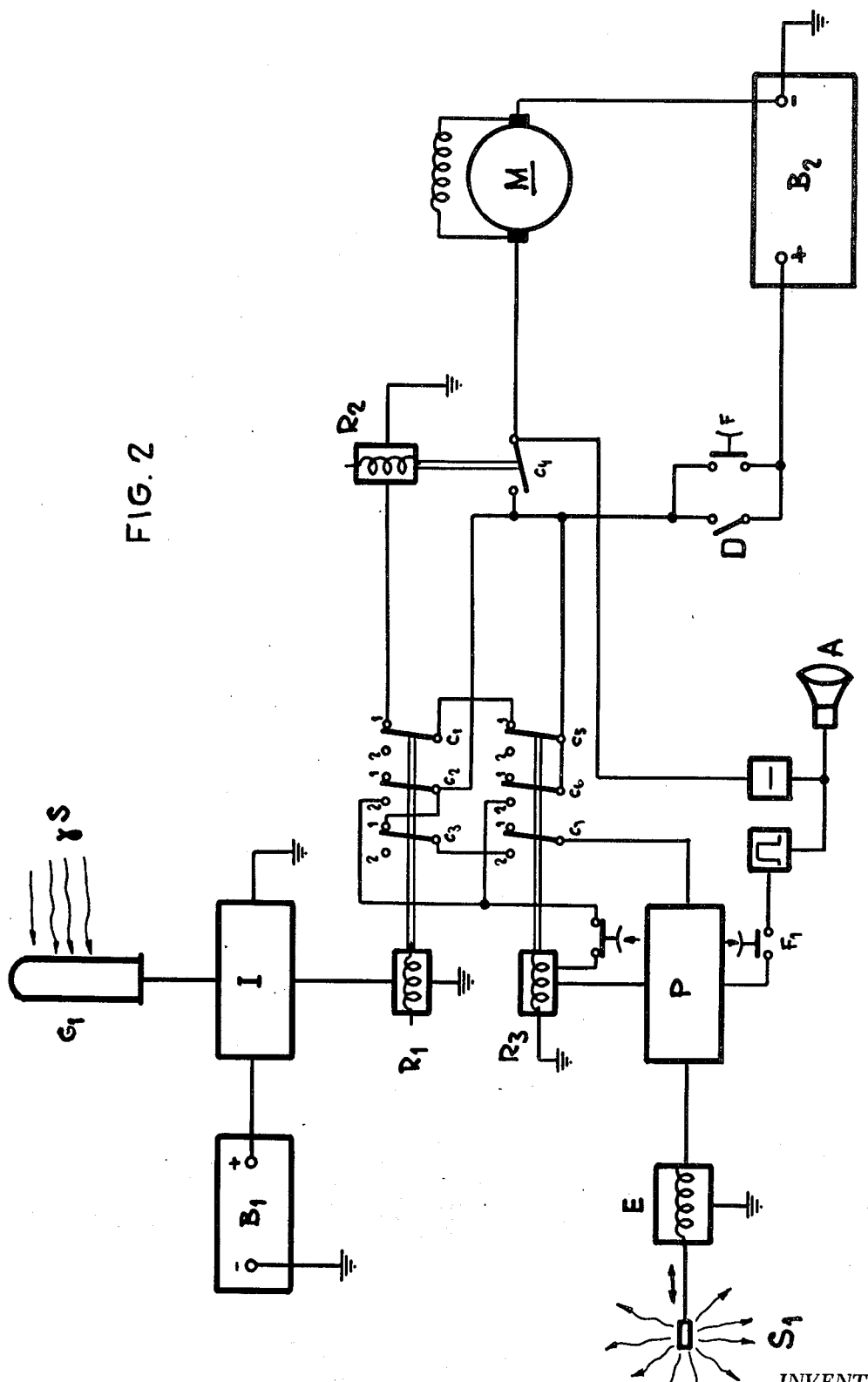

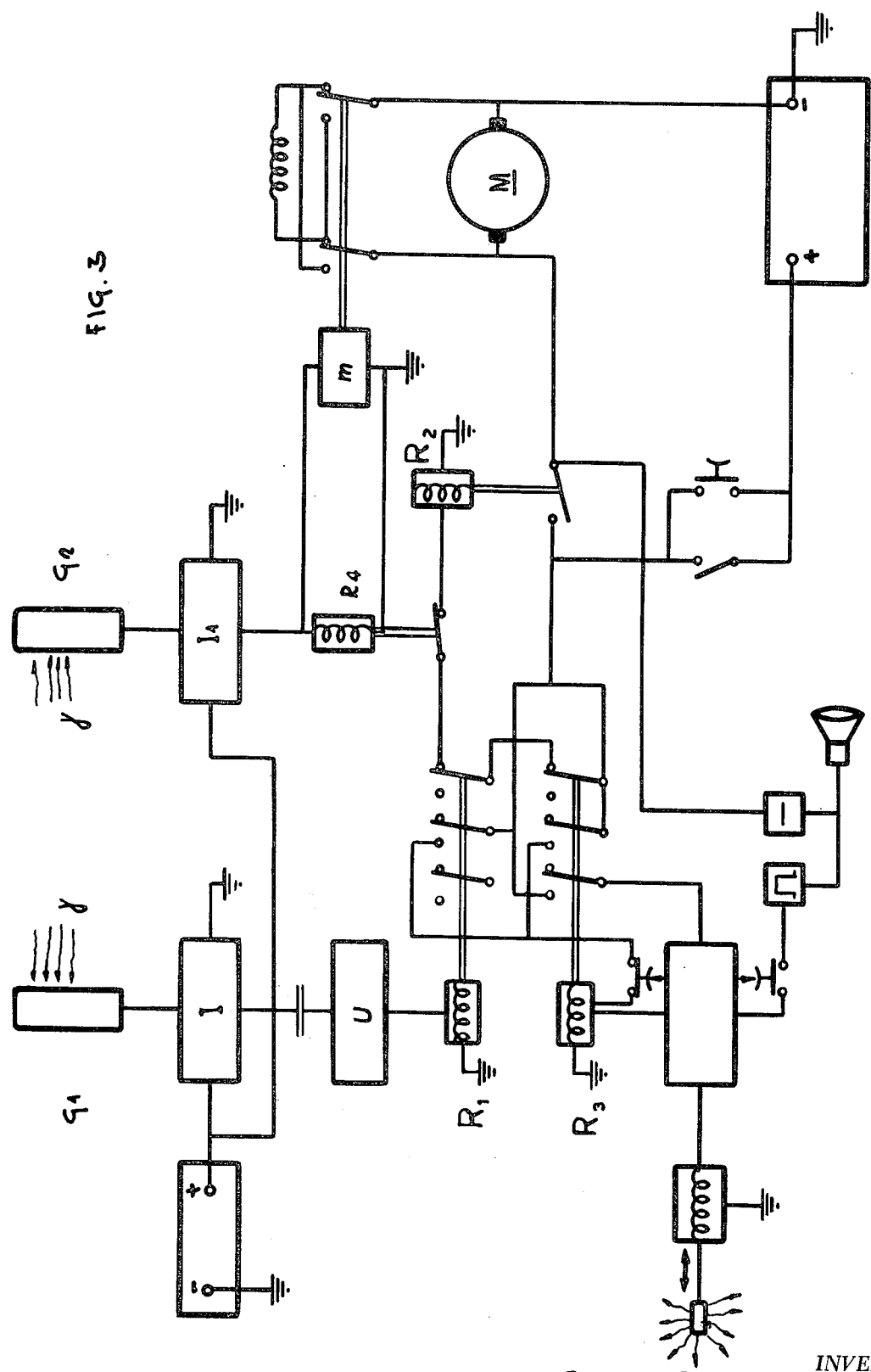

DEVICE FOR THE PANORAMIC RADIOGRAPHY OF WELDINGS IN METAL PIPINGS

This is a continuation of application of Ser. No. 303,684, filed Nov. 6, 1972; and a continuation of application Ser. No. 163,503, filed July 16, 1971; and a continuation of Ser. No. 18,564, filed Mar. 11, 1970; all now abandoned.

A principal object of the present invention is the provision of a device which allows the radiography of welds in metal pipes. The importance of radiographing the metal welds in order to verify their good execution is known. This requirement is particularly apparent in the case of metal pipes, and more particularly in pipe systems known as "pipelines" and "sea lines".

For the last cases, attempts have been made to solve the problem in a more or less satisfactory way by resorting to different solutions. In general, use has been made of devices able to move inside the pipes and to execute by means of suitable controls, the radiography of the zone under inspection. The device of the present invention affords, in comparison with the known ones, noticeable advantages simultaneously, as, for example, the ability to reach, with extreme precision, the zone to be radiographed, the possibility to radiograph at one time the whole zone of welding and all this in conditions of utmost safety for the operators. The device includes a mobile system which is able to run through the pipe under examination. The system uses a radiation source for the radiography and has a device for detecting radiations as, for example, the one known as Geiger-Muller counter. The Geiger-Muller counter is controlled by a radiation source located outside the pipe (and positioned by an operator) to stop and locate the apparatus in the position where the radiography must be executed.

The new and original characteristics of the device of the present invention are obtained by means of a series of combined elements in order to provide:

the stopping of the device in the desired position;

the necessary starting of a program system which allows the execution of the operation which is of interest in the specific case;

the self adjustment of said device on the bottom of the pipe for the whole period of its operation.

Therefore in a diagrammatic form the device of the present invention comprises a mobile system driven by batteries, a receiver of radiations, such as a Geiger counter, which, under the action of an outside radiation source (during the approaching to the outside wall of the pipe) stops the mobile system at the zone to be radiographed. The counter allows, upon removal of said source, which was positioned on the outside wall of the pipe, the starting of a programmed system which controls the operations of: preparation for radiography of a second source of radiation incorporated in the device, by moving the source from a safety container up to a zone suitably diaphragmed which allows the radiation to cross the welding zone in a direction transverse to the length of the pipe; exposition of said zone to radiations for a period sufficient to carry out the radiography (the receiving system sensitive to radiations, like e.g. a sensitive film being located outside the piping); re-entering thereafter of the source into a safety container (such a re-entering is carried out in any case by an automatic device) and, once the above mentioned operations, have been completed starting of the mobile system in the usual running direction. It is possible, of course, to reverse the running direction by providing the apparatus with a second Geiger.

An acoustical system in the device is also contemplated to trace the different phases of the operation during their execution.

The self-setting of the device is accomplished by a pendulum which drives the front wheels, said pendulum being constituted by the weight of the same batteries which provides the energy to enable the carriage to travel on the pipe bottom. The pendulum enables the device to follow the bending radius without overturning.

The main elements constituting the device (vehicle) and their function are specified hereinafter.

Driving pendulum

The driving pendulum is formed by a plane having a sectional shape which carries the battery and is guided by two traverses which permit the adjustment of the steering in a plane. Four vertically profiled rods connect the plane of the battery to the upper hinge supporting the pendulum and allowing it to rock transversally to the vehicle carriage so as to keep the battery always normal to the plane whatever the conditions of the carriage wheels will be.

The pendulum of this type performs two important functions:

a. the battery is always in a position perpendicular to the plane thereby preventing the overpouring of the electrolytic liquid.

b. the pendulum is coupled with a set of levers to the steering to permit the automatic guide of carriage on the pipe bottom and thereby avoiding the screwing of the carriage into the pipe (pipeline or sealine).

Regulation of the wheels

The front wheels of the carriage are steering wheels, driven by the pendulum. These wheels allow the carriage to travel on the bottom and to follow the pipeline bends, otherwise at the corners the carriage would tend to climb along the pipe tangentially. But the pendulum remains in a position perpendicular to the plane and thereby steers the wheels to allow the carriage to bend and follow the contour of the pipeline bottom without drawbacks.

The steering-gear is controlled in plane by shifting the barycenter of the pendulum in such a way that the carriage travels in an upright orientation this is an operation carried out only in a testing phase.

Control of the source for the radiography

The source is housed in a special shield and is driven into exposition by an electro-magnet which sets the source between two circular crowns which collimate the $\gamma$-rays over an angle of 360°.

The re-entry of the source in the shield occurs by means of a calibrated spring that allows, if there is an electric breakdown, the automatic re-entry of the source into a special container.

Source container

The source container is provided in such a way that during exposition the $\gamma$-activity is considerably reduced in the axial direction (in front and at the back of the device). Thus the operator may continue his work due to the fact that in the front part of the device (vehicle) a shield has been assembled. The shield is formed of shielding material which allows the γ-rays collimation in the direction of the weld to be radiographed and provides protection of the operators working in front of the carriage. In the back side of the device (vehicle) the same source container, which protects the operators, collimates the γ-rays.

Acoustic signalling

An acoustic warning device indicates continuously the position of the vehicle while in motion without resorting to devices like a G.M. counter and is silent when the carriage is under the positioning source.

The acoustic frequency is a function of the battery voltage of the motor so that the battery charge may be checked from the outside with a special device able to measure an acoustic frequency.

When the positioning γ-source is taken away, the intermittent acoustic signal starts advancing the source exposition by 40 seconds. This time is necessary to allow the operators to assume a safe distance from the device.

The intermittent signal is silent shortly after the source has been enclosed within the source container.

DESCRIPTION OF THE DRAWINGS

FIG. 2 is a circuit diagram for use operating the device shown in FIG. 1; and

FIG. 3 is an alternate circuit diagram, similar to that shown in FIG. 2, and adapted for use in the device of the present invention.

With reference to FIG. 1, the reference numerals represent respectively:

Figure 1:
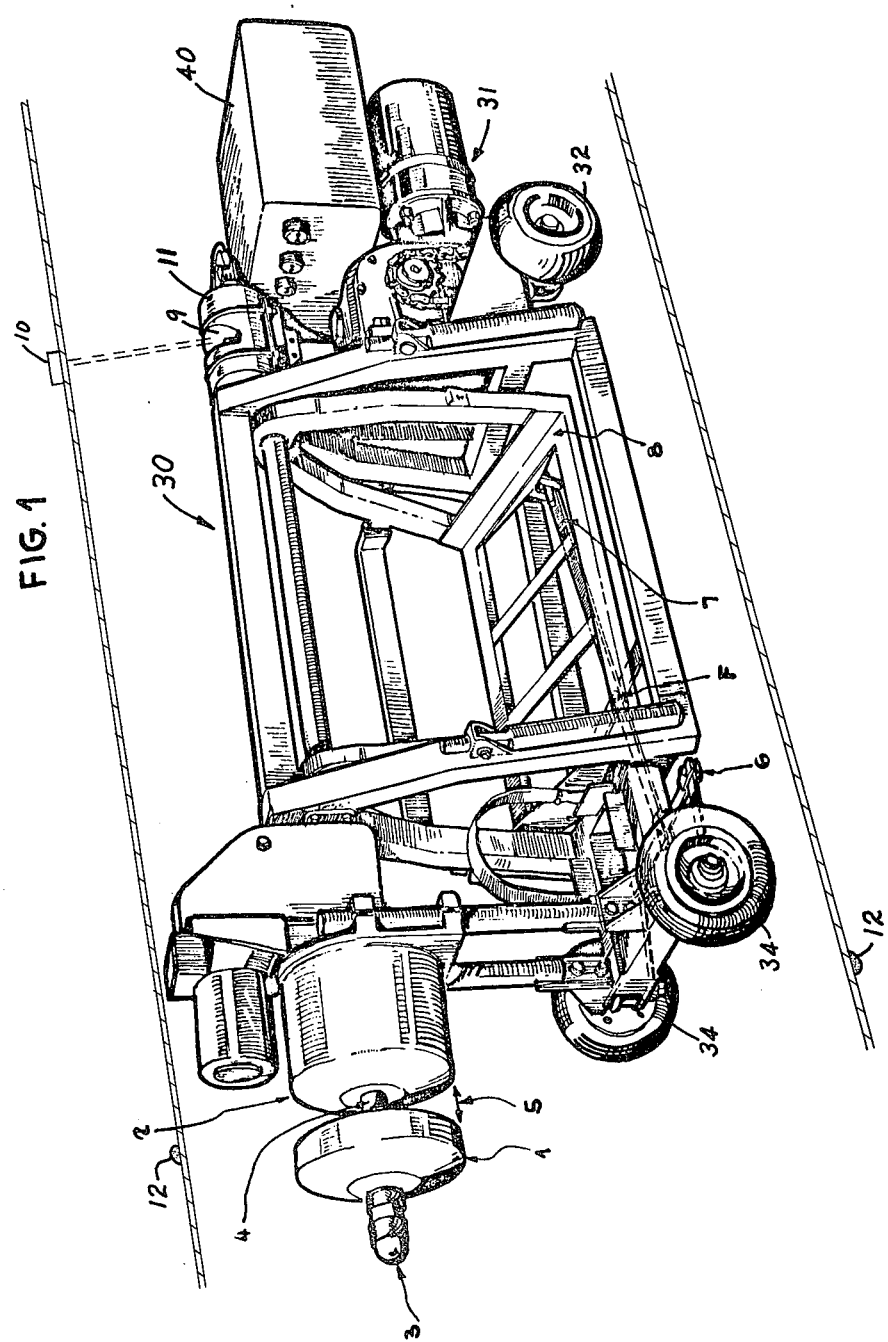
FIG. 1 is a perspective view of a device in accordance with the present invention, and showing the device within a pipeline.

1, front diaphragm of inside radiation source
2, back diaphragm of radiation source and safety container
3, screw cup for hollow cylinder 4 wherein the radiation source slides
5, collimation zone of radiation source
6, transmission parallelogram driving the steering wheels by means of rod 7 pivotally mounted to frame F and driven by the battery support 8 which forms a pendulum
9, window for collimating the incident ray of an outside source 10, with Geiger-Mueller counter 11.

The device according to the invention comprises substantially two essential parts:

1. Self-propelled carriage 30 moved by a D.C. geared motor 31 powered by lead-batteries. The geared motor moves the carriage back wheels 32 while the front wheels 34 are directional and driven by a pendulum carrying the batteries allowing the carriage to run on the pipe bottom and to follow the bending radius without overturning.

The radioisotope is housed on the carriage inside a special shaped lead shield which permits, by means of an electro-magnet, the radioisotope exposition for the panoramic radiography.

2. Driving electronic device 40. It may be provided in many ways and therefore it will be now a illustrated only for two particular cases:

a. the first type, FIG. 3, is the one more complete type and allows the vehicle the following operations: running — stop — exposition — reverse motion (very useful in laying sea-lines).

b. the second type, FIG. 2, is the simpler type and allows the vehicle the following operations: running — stop — exposition.

The same driving system is used for the two types and includes a low intensity radioactive source located outside of the pipe which irradiates the G.M. counters suitably arranged on the vehicle.

Operation of the first type

In this type two G.M. (Geiger-Mueller) counters G1 and G2 are arranged on the vehicle and housed suitably in lead containers having a window for collimating the incident rays one of said counters being directed upwards, the other one downwards.

The carriage is set in the pipe (pipeline), started and moves so long as it does not meet, near the weld, the driving source 10 which is housed in a lead container having a collimation window of a few millimeters.

When the two windows of the source 10 and of the G.M. counter 11 collimate, the γ-rays irradiate the Geiger counter which, by an electronic circuit, stops the vehicle and begins the preexposition program. The start of the program is signalled by an intermittent acoustic signal allowing the operator to move array a safe distance. The signal preceeds the radioisotope exposition for the panoramic radiography by 40 seconds.

The exposition time, for a given source, is allowed to vary, according to the type of sensitive plate and according to the pipe diameter, by means of a special timer. When the exposition is ended, the intermittent acoustic signal stops and the vehicle starts whether or not the source has been taken away.

The cycle described is repeated for every weld.

The second G.M. counter G2 having the collimation window directed downwards is used when it is necessary to stop the vehicle inside the pipeline or to reverse its running.

Once the driving source is positioned upwards the vehicle stops and no exposition occurs during the permanence of the driving source; when the source is taken away the vehicle reverses its running.

If we want the vehicle to assume the initial running, a second arrangement of the source has to be made like the previous one.

Operation of the second type

In this type, FIG. 2, a single G.M. counter G1 is arranged on the vehicle. This counter is housed inside a lead container having a collimation window 9 directed upwards. The carriage is introduced into the pipe (pipeline) and started by hand. The device moves and emits a continuous acoustic signal so long as it does not meet the positioning source 10 near the weld. The source is like the one previously specified. When the two windows of the source 10 and of the G.M. counter G1 collimate, the γ-rays irradiate the Geiger counter which, by means of an electronic circuit, stops the vehicle during the time the source irradiates the G.M. counter, and terminates the acoustic continuous signal.

If it is desired to carry out the panoramic exposition of the source for the radiography, it is sufficient to take away the control source and the exposition cycle is performed as previously described.

An example of an electric circuit suitable for the device of the second type according to the invention is shown in FIG. 2.

In said figure S represents the radiation source 10 outside the pipeline. Radiation falls on the Geiger counter G 1 which produce a succession of pulses which reach the integrator system I. The output of system I controls a relay $R_1$ which, moves the contacts $C_1$ from rest position 1 to position 2 (shown in figure). In this way the carriage is stopped as the relay $R_2$ opens the contact $C_4$ ($B_1$ is a battery for feeding the electronic circuits, $B_2$ is a battery for feeding the carriage motors). The shifting of contact $C_2$ by relay $R_1$ from the position 1 to 2 charges relay $R_3$ which returns the contacts $C_5$ $C_6$ $C_7$ to positions 2. When contact $C_3$ passes from 1 to 2, the operating control P is interrupted. The contact $C_5$, now in position 2, acts in series with contact C, such that the carriage does not move even if the source is taken away or the contact $C_1$ goes back to position 2. The contact $C_6$ in position 2 maintains $R_3$ excited; contact $C_7$ in position 2 prepares the programmer P. In this condition taking away the source S, the relay $R_1$ is de-energized. The programmer P receives the operating control through contacts $C_3$ and $C_7$ and starts the preexposition program of inside source radiation $S_1$ (for radiography) and modulates the acoustic signal coming out from A. After a determined time the programmer energizes the electro-magnet E which removes the radio-active source from the container 2, leaves it for a determined time and then the returning system operates to bring the source back into the container. In these conditions $F_1$ stops the modulated acoustic signal and restores the original sound. The relay $R_3$ is de-energized the vehicle starts again and is prepared for a new the cycle.

At the beginning of all the above mentioned operations, the interrupter D is inserted and the device is prepared to carry out said operations. At the same time a continuous signal shows that the carriage is moving through the pipe; the absence of sound indicates that the stop of the device has stopped and the modulated signal indicates that the programmed operations have started. F represents a push-button for the manual operations when the electronic device is switched off. When $B_1$ is below a determined level of charge, the electronic device is disconnected, does not reply to the external orders and the vehicle goes ahead by itself in the running direction. In FIG. 3 it is shown the wiring diagram representing the first type (above specified) wherein the carriage has two running directions.

The circuit is illustrated in a way like the one shown in FIG. 2 except for the following differences:

The integrator I drives in A.C. the relay $R_1$ by means of an univibrator U, therefore, when relay $R_1$ is closed, $R_3$ is closed too and the program with the above mentioned cycles starts. Once the program is ended, the vehicle starts. This occurs whether or not the control source 10 is taken away.

A second electrical channel is coupled to the previous one. Geiger Counter G2 is connected to the channel to provide an input signal thereto. This channel orders the stop of the vehicle and stores the reverse running mode by means of integrator $I_1$ and $R_4$. Element $m$ stores the reversal of the running of the vehicle.

Referring to the Figures and to the present specification, it is clear that changes may be made by those skilled in the art without departing from the scope of the present invention.

The changes could concern the use of equivalent electrical circuits suitable to operate in a similar way, and the simplification and modification of running in order to solve functions different from the ones carried out by the device according to the invention. Besides the panoramic radiography the device according to the invention, with simple variants within the range of the skilled in the art, could be used e.g. for the pipe cleaning, pipe painting. In spite of the fact that the device, used in the field of the panoramic radiography, has been specified as making use of γ-rays, it is clear that it could make use of different rays, e.g. x-rays.

We claim:

1. Apparatus for radiographing welds from the inside of a pipeline comprising: (a) carriage means including a two wheel drive system arranged to propel the carriage means inside the pipeline; two wheel means for steering and maintaining the travel of the carriage on the bottom of the pipeline; (b) a radiography source; a safety, radiation impervious housing for said radiography source including first and second shield diaphragms defining a 360° panoramic exposition zone transversely to the pipeline; a spring loaded electromagnet for reciprocally moving the radiography source axially between said diaphragms for exposition and the safety housing, the spring loaded electromagnet normally biasing the source to a safety position within the safety housing; (c) means mounted on said carriage means for selectively stopping the carriage at a location to be radiographed including a GM counter positioned to receive radiation from a source located outside the pipeline at said location; circuit means operatively coupled to the GM counter to receive a signal input therefrom including a programmer for energizing said source electromagnet, said circuit means including means for terminating power to said drive means to stop the carriage, and energizing the programmer, said programmer being operatively coupled to energize a pulsating acoustical alarm for a predetermined period prior to energizing said source electromagnet.

2. Apparatus of claim 1 wherein said two wheel drive system includes a power source mounted on the carriage means.

3. Apparatus of claim 1 wherein said G.M. counter includes means defining a collimating window, said window being defined by a vertical wall and an inclined wall opposite said vertical wall.

4. Apparatus of claim 1 wherein said two wheel steering and maintaining means includes a pair of front wheels articulately mounted to the carriage means; said front wheels arranged to be driven by a transmission parallelogram connected to a pendulum constituted by a platform supported by vertical rods from a hinge on the carriage means which allows the pendulum to rock transversely thereto and maintains the platform normal to the horizontal plane, said front wheels being deflected in one direction when the pendulum is deflected in the other direction.

* * * * *